United States Patent
Imamura (10) Patent No.: US 10,388,012 B2
(45) Date of Patent: Aug. 20, 2019

(54) IMAGE PROCESSING APPARATUS, IMAGE PROCESSING METHOD, AND PROGRAM FOR IDENTIFYING CELLS OF BLOOD VESSEL WALL

(71) Applicant: CANON KABUSHIKI KAISHA, Tokyo (JP)

(72) Inventor: Hiroshi Imamura, Kawasaki (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 15/545,346

(22) PCT Filed: Mar. 23, 2016

(86) PCT No.: PCT/JP2016/060287
§ 371 (c)(1),
(2) Date: Jul. 21, 2017

(87) PCT Pub. No.: WO2016/153075
PCT Pub. Date: Sep. 29, 2016

(65) Prior Publication Data
US 2018/0012353 A1    Jan. 11, 2018

(30) Foreign Application Priority Data
Mar. 25, 2015    (JP) .................. 2015-062507

(51) Int. Cl.
*G06K 9/00*    (2006.01)
*G06T 7/00*    (2017.01)
(Continued)

(52) U.S. Cl.
CPC .......... *G06T 7/0012* (2013.01); *A61B 3/0025* (2013.01); *A61B 3/1225* (2013.01);
(Continued)

(58) Field of Classification Search
CPC ......... G06T 7/0012; G06T 2207/30041; G06T 2207/30104; G06T 7/0016; G06T 7/248
See application file for complete search history.

(56) References Cited

U.S. PATENT DOCUMENTS 6,840,933 B1 *  1/2005  Pang .................... A61B 3/1241
                                                                600/479
8,840,248 B2    9/2014  Imamura
(Continued)

OTHER PUBLICATIONS

Sep. 26, 2017 International Preliminary Report on Patentability in International Patent Appln. No. PCT/JP2016/060287.
(Continued)

*Primary Examiner* — Vu Le
*Assistant Examiner* — Guillermo M Rivera-Martinez
(74) *Attorney, Agent, or Firm* — Venable LLP (57) ABSTRACT

Provided is an image processing apparatus configured to process an image of a fundus of an eye, which is capable of simply and accurately measuring a distribution of cells that form a blood vessel wall of an eye. The image processing apparatus includes: an image acquiring unit configured to acquire an image of an eye; a vessel feature acquiring unit configured to acquire membrane candidate points that form an arbitrary wall of a blood vessel based on the acquired image; and a cell identifying unit configured to identify a cell that forms the wall of the blood vessel based on the membrane candidate points.

10 Claims, 8 Drawing Sheets

(51) Int. Cl.
  *G06T 7/12* (2017.01)
  *A61B 3/00* (2006.01)
  *A61B 3/12* (2006.01)

(52) U.S. Cl.
  CPC ...... *G06T 7/12* (2017.01); *G06T 2207/10056* (2013.01); *G06T 2207/30041* (2013.01); *G06T 2207/30101* (2013.01)

(56) References Cited

U.S. PATENT DOCUMENTS

| | | | |
|---|---|---|---|
| 8,861,817 B2 | 10/2014 | Imamura et al. | |
| 9,098,742 B2 | 8/2015 | Yonezawa et al. | |
| 9,307,903 B2 | 4/2016 | Imamura | |
| 9,320,424 B2 | 4/2016 | Imamura | |
| 9,351,650 B2 | 5/2016 | Uji et al. | |
| 9,355,446 B2 | 5/2016 | Imamura et al. | |
| 2003/0096302 A1* | 5/2003 | Yguerabide | C12Q 1/6816 435/7.1 |
| 2007/0167718 A1* | 7/2007 | Kaufman | A61B 5/055 600/407 |
| 2011/0098685 A1* | 4/2011 | Flower | A61K 9/5063 604/890.1 |
| 2011/0137157 A1 | 6/2011 | Imamura et al. | |
| 2011/0287948 A1* | 11/2011 | Suresh | B01L 3/502746 506/7 |
| 2011/0301441 A1* | 12/2011 | Bandic | A61B 5/0059 600/306 |
| 2012/0218516 A1* | 8/2012 | Imamura | A61B 3/1025 351/206 |
| 2014/0085606 A1 | 3/2014 | Miyasa et al. | |
| 2014/0240667 A1 | 8/2014 | Uji et al. | |
| 2014/0333749 A1 | 11/2014 | Imamura | |
| 2014/0354794 A1 | 12/2014 | Imamura | |
| 2014/0362344 A1 | 12/2014 | Imamura | |
| 2016/0067357 A1* | 3/2016 | Francois | C12Q 1/37 424/9.6 |
| 2016/0235290 A1 | 8/2016 | Imamura et al. | |

OTHER PUBLICATIONS

Toco Y.P. Chui, et al., "Imaging of Vascular Wall Fine Structure in the Human Retina Using Adaptive Optics Scanning Laser Ophthalmoscopy," Investigative Ophthalmology & Visual Science, vol. 54, No. 10, Oct. 29, 2013, pp. 7115-7124.

Edouard Koch, et al., "Morphometric analysis of small arteries in the human retina using adaptive optics imaging: relationship with blood pressure and focal vascular changes," Journal of Hypertension, vol. 32, No. 4, Apr. 2014, pp. 890-898.

Nicolas Lermé, et al., "Segmentation of Retinal Arteries in Adaptive Optics Images," 2014 22nd International Conference on Pattern Recognition, IEEE Computer Society, Aug. 24, 2014, pp. 574-579.

Toco Y.P. Chui, et al., "The use of forward scatter to improve retinal vascular imaging with an adaptive optics scanning laser ophthalmoscope," Biomedical Optics Express, vol. 3, No. 10, Oct. 1, 2012, pp. 2537-2549.

Jul. 19, 2016 International Search Report and Written Opinion in International Patent Appln. No. PCT/JP2016/060287.

* cited by examiner

IMAGE PROCESSING APPARATUS, IMAGE PROCESSING METHOD, AND PROGRAM FOR IDENTIFYING CELLS OF BLOOD VESSEL WALL

TECHNICAL FIELD

The present invention relates to an image processing apparatus, an image processing method, and a program therefor, which are to be used for ophthalmic diagnosis and treatment.

BACKGROUND ART

The inspection of an eye has been widely conducted for the purpose of diagnosing and treating lifestyle-related diseases and diseases that are leading causes of blindness in early stages. As an ophthalmic apparatus to be used for the inspection of the eye, there is a scanning laser opthalmoscope (SLO) using a principle of a confocal laser microscope. The scanning laser opthalmoscope is an apparatus configured to perform raster scanning on a fundus of an eye with laser light that is measuring light to obtain a planar image of the fundus based on the intensity of return light of the measuring light, and the image is obtained with high resolution at high speed. Further, in the scanning laser opthalmoscope, the planar image is generated by detecting only light having passed through an aperture portion (pinhole) out of the return light. This allows only return light at a particular depth position to be imaged, and an image having a contrast higher than that of a fundus camera or the like to be acquired. Such an apparatus configured to photograph a planar image is hereinafter referred to as "SLO apparatus", and the planar image is hereinafter referred to as "SLO image".

In recent years, in the SLO apparatus, it has become possible to acquire an SLO image of a retina with improved lateral resolution by increasing a beam diameter of measuring light. However, along with the increase in the beam diameter of the measuring light, an S/N ratio and the resolution of an SLO image of a retina decrease due to an aberration of an eye to be inspected when the SLO image is acquired. The decreases in the resolution are handled by measuring an aberration of an eye to be inspected by a wavefront sensor in real time, and by correcting aberrations of measuring light and return light thereof generated in the eye to be inspected by a wavefront correction device. An adaptive optics SLO apparatus including an adaptive optics system such as the wavefront correction device has been developed to enable the acquisition of an SLO image having a high lateral resolution.

Figure 6A:
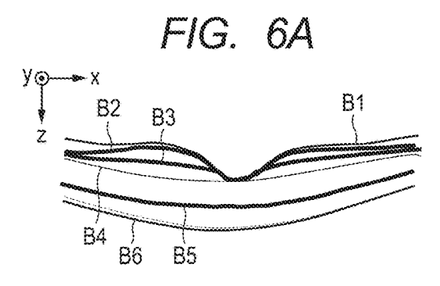
FIG. 6A is a diagram for illustrating details of image processing according to the embodiment of the present invention, and illustrating an imaged layer structure of a retina.
Figure 6B:
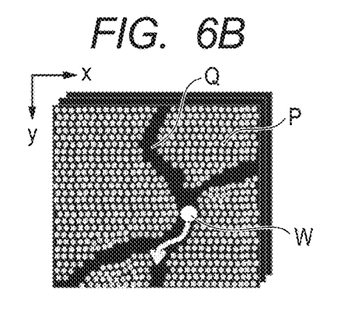
FIG. 6B is a diagram for illustrating an example of an SLO image obtained by an adaptive optics SLO apparatus.

The SLO image obtained by the adaptive optics SLO apparatus can be acquired as a moving image. Therefore, for example, in order to observe hemodynamics non-invasively, the SLO image is used for measurement of the moving speed of blood corpuscles in a capillary vessel and the like through extraction of a retinal vessel from each frame. Further, in order to evaluate a relation with a visual function through use of the SLO image, a density distribution and arrangement of photoreceptor cells P are also measured through detection of the photoreceptor cells P. FIG. 6B is an illustration of an example of the SLO image with a high lateral resolution obtained by the adaptive optics SLO apparatus. In the image, the photoreceptor cells P, a low brightness region Q corresponding to the position of the capillary vessel, and a high brightness region W corresponding to the position of a leukocyte can be observed.

In a case of observing the photoreceptor cells P in such an SLO image, a focus position is set to the vicinity of an outer layer of the retina (for example, layer boundary B5 in FIG. 6A), to thereby acquire such an SLO image as illustrated in FIG. 6B. Meanwhile, retinal vessels and branching capillary vessels travel in an inner layer of the retina (from layer boundary B2 to layer boundary B4 in FIG. 6A). When an adaptive optics SLO image is acquired with the focus position set in the inner layer of the retina, for example, a retinal vessel wall can be observed directly.

However, in a confocal image obtained by imaging the inner layer of the retina, a noise signal is strong due to the influence of light reflected from a nerve fiber layer, and hence it is difficult to observe a blood vessel wall and detect a wall boundary in some cases. In view of the foregoing, in recent years, a method involving obtaining scattering light by changing the diameter, shape, and position of a pinhole arranged in front of a photo-receiving unit and observing a nonconfocal image thus obtained has come to be used (Non Patent Literature 1 (NPL 1)). In the nonconfocal image, a focus depth is large, and hence an object having irregularities in a depth direction, such as a blood vessel, can be observed easily. Further, light reflected from the nerve fiber layer is not easily received directly, and hence noise can be reduced.

Meanwhile, a retinal artery is an arteriole having a blood vessel diameter of from about 10 μm to about 100 μm, and a wall of the retinal artery is formed of an intima, a media, and an adventitia. Further, the media is formed of smooth muscle cells, and travels along a circumferential direction of the blood vessel in a coil shape. Against a backdrop of hypertension or the like, when pressure exerted on the wall of the retinal artery increases, a smooth muscle contracts to increase a wall thickness. At this point in time, when blood pressure is lowered through administration of an antihypertensive agent, the shape of the wall of the retinal artery returns to an original shape. However, when the hypertension remains untreated for a long period, the smooth muscle cell that forms the media undergoes necrosis, and fibrous hypertrophy of the media and the adventitia occurs to increase the wall thickness. At this point in time, an organic (irreversible) dysfunction has already occurred in the wall of the retinal artery, which necessitates continuous treatment so as to prevent an arteriole dysfunction from becoming worse.

Hitherto, a technology for acquiring the nonconfocal image of the retinal vessel through use of the adaptive optics SLO apparatus and visualizing the retinal vessel wall cells is disclosed in NPL 1. In addition, a technology for semiautomatically extracting a retinal vessel wall boundary from an image of an adaptive optics fundus camera through use of a variable shape model is disclosed in Non Patent Literature 2 (NPL 2).

The presence or absence and degree of an organic change in the arteriole need to be estimated in the body of a person suffering hypertension, diabetes, or the like. Therefore, it is desired to simply and accurately measure shapes and distributions relating to the walls, membranes, and cells of the retinal artery being an only tissue that can be observed directly among the arterioles of the entire body. However, in an actual case, the wall thickness and membrane thickness of the retinal artery and the distribution of wall cells of the retinal artery are manually measured from the image acquired through use of an SLO apparatus to which an adaptive optics technology is applied. Therefore, the measurement is complicated, and includes a measuring error caused by an operator, which raises a problem of low reproducibility.

In the technology disclosed in NPL 1, the retinal vessel wall, the membrane boundary, and the wall cells are visualized from an AO-SLO image having a nonconfocal image acquisition function based on pinhole control, and the membrane thickness and a cell density are manually measured. However, a technology for automatically measuring the wall thickness and membrane thickness of the retinal vessel and the density of cells that form the wall is not disclosed.

In the technology disclosed in NPL 2, the retinal vessel wall boundary is detected from the image of the adaptive optics fundus camera through the use of the variable shape model, and the wall thickness of the retinal artery is semi-automatically measured. However, a venous wall, or membranes or cells that form an arterial wall and a venous wall cannot be visualized from the image of the adaptive optics fundus camera. That is, a technology for measuring the wall thickness of a vein, the membrane thickness of the artery or the vein, or the distribution of wall cells is not disclosed even in NPL 2.

Accordingly, there is a demand for a technology for automatically measuring the wall thickness, the membrane thickness, and the distribution of the cells that form the wall from the image obtained by visualizing the blood vessel wall of the eye and the membranes and cells that form the blood vessel wall.

CITATION LIST

Non Patent Literature

NPL 1: Chui et al.; "Imaging of Vascular Wall Fine Structure in the Human Retina Using Adaptive Optics Scanning Laser Ophthalmoscopy", IOVS, Vol. 54, No. 10, pp. 7115-7124, 2013.
NPL 2: Koch et al.; "Morphometric analysis of small arteries in the human retina using adaptive optics imaging: relationship with blood pressure and focal vascular changes", Journal of Hypertension, Vol. 32, No. 4, pp. 890-898, 2014.

SUMMARY OF INVENTION

Technical Problem

The present invention has been made in view of the above-mentioned problems, and has an object to provide an image processing apparatus, an image processing method, and a program therefor, which enable automatic measurement of the distribution of cells that form a blood vessel wall of an eye.

Solution to Problem

In order to attain the above-mentioned object, according to one embodiment of the present invention, there is provided an image processing apparatus, including:
an image acquiring unit configured to acquire an image of an eye;
an acquiring unit configured to acquire membrane candidate points that form an arbitrary wall of a blood vessel based on the acquired image; and
a cell identifying unit configured to identify a cell that forms the wall of the blood vessel based on the membrane candidate points.

Further, according to one embodiment of the present invention, there is provided an image processing method, including:

acquiring an image of an eye;
a vessel feature acquiring step of acquiring membrane candidate points that form an arbitrary wall of a blood vessel based on the acquired image; and
identifying a cell that forms the wall of the blood vessel based on the membrane candidate points.

Advantageous Effects of Invention

According to the present invention, it is possible to simply and accurately measure the distribution of the cells that form the blood vessel wall of the eye.

Further features of the present invention will become apparent from the following description of exemplary embodiments with reference to the attached drawings.

DESCRIPTION OF EMBODIMENTS

Now, an image processing apparatus and an image processing method according to an exemplary embodiment of the present invention are described in detail with reference to the accompanying drawings. Note that, the following embodiments are not intended to limit the present invention defined in the appended claims, and not all combinations of features described in the embodiments are essential to solving means of the present invention.

First Embodiment

An image processing apparatus according to a first embodiment of the present invention uses an image obtained by imaging a retinal vessel wall through use of an SLO apparatus configured to simultaneously acquire a confocal image and a nonconfocal image. A brightness distribution along a travel direction of the wall, that is, a vessel travel direction, or an extreme value of a brightness profile is detected from the image. Then, wall cells are detected based on the obtained extreme value, and a distribution thereof is automatically measured.

Specifically, the retinal vessel wall is imaged through use of the SLO apparatus configured to simultaneously acquire a confocal image and a nonconfocal image. A center line of a retinal vessel (hereinafter referred to also as "blood vessel center line") is acquired from the obtained nonconfocal image by morphology filter processing. A membrane candidate region that forms the retinal vessel wall is further acquired based on the blood vessel center line. Then, a brightness profile along the travel of a blood vessel wall is generated based on the membrane candidate region. A brightness value within the brightness profile is subjected to a Fourier transform. After a high frequency component is removed from the image that has been subjected to the Fourier transform, a peak position within the brightness profile is detected as the position of the wall cells. A wall cell density is measured based on the detected peak position or the like. In the following, the embodiment of a case of executing such an operation is described.

(Overall Configuration)

Figure 2:
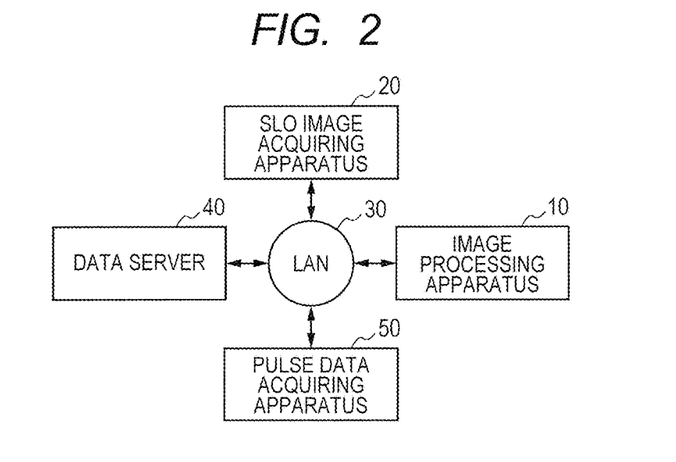
FIG. 2 is a block diagram for illustrating a configuration example of a system including the image processing apparatus according to the embodiment of the present invention.

FIG. 2 is a diagram of an overall configuration of a system including an image processing apparatus 10 according to this embodiment. As illustrated in FIG. 2, the image processing apparatus 10 is connected to an SLO image acquiring apparatus 20, a data server 40, and a pulse data acquiring apparatus 50 through a local area network (LAN) 30. The LAN 30 is formed of an optical fiber, USB, IEEE 1394, or the like. Note that, the connection to those apparatus may be configured as the connection through an external network such as the Internet. Alternatively, the direct connection to the image processing apparatus 10 may be employed.

The SLO image acquiring apparatus 20 is an apparatus configured to acquire a wide field angle image Dl of an eye and a confocal image Dc and a nonconfocal image Dn that are high magnification images. The SLO image acquiring apparatus 20 transmits the wide field angle image Dl, the confocal image Dc, the nonconfocal image Dn, and information on fixation target positions Fl and Fcn used at a time of image acquisition thereof to the image processing apparatus 10 and the data server 40. Note that, the SLO image acquiring apparatus 20 functions as an image acquiring unit configured to acquire the image of the eye in this embodiment.

The pulse data acquiring apparatus 50 is an apparatus configured to acquire biosignal data (pulse data) that changes autonomously, and is formed of, for example, a sphygmograph or an electrocardiograph. The pulse data acquiring apparatus 50 acquires pulse data Pi simultaneously with the acquisition of the wide field angle image Dl, the confocal image Dc, and the nonconfocal image Dn in response to an operation performed by an operator (not shown). The obtained pulse data Pi is transmitted to the image processing apparatus 10 and the data server 40. Note that, the pulse data acquiring apparatus 50 may be directly connected to the SLO image acquiring apparatus 20.

Note that, when the respective images are acquired in different image-acquiring positions, a plurality of images are respectively represented by, for example, Dli, Dcj, and Dnk. That is, i, j, and k are variables each representing an image-acquiring position number, and are set as i=1, 2, . . . , and imax, j=1, 2, . . . , and jmax, and k=1, 2, . . . , and kmax. Further, when the confocal images Dc (nonconfocal images Dn) are acquired with different magnifications, the images are represented by Dc1$m$, Dc2$o$, . . . (Dn1$m$, Dn2$o$, . . . ) in descending order of the magnification. Further, Dc1$m$ (Dn1$m$) is represented by a high magnification confocal (nonconfocal) image, and Dc2$o$, . . . (Dn2$o$, . . . ) is represented by a medium magnification confocal (nonconfocal) image.

The SLO image acquiring apparatus 20 transmits the wide field angle image Dl, the confocal image Dc, the nonconfocal image Dn, the fixation target positions Fl and Fcn used at the time of the image acquisition, the pulse data Pi, and the like to the data server 40. The data server 40 stores those pieces of information along with image features of the eye output by the image processing apparatus 10. The fixation target positions Fl and Fcn are fixation target positions used at the time of the image acquisition, and it is preferred that other image-acquiring conditions be also stored along with those fixation target positions. Examples of the image features include features regarding the retinal vessel, the retinal vessel wall, and the wall cells. Further, in response to a request made by the image processing apparatus 10, the wide field angle image Dl, the confocal image Dc, the nonconfocal image Dn, the pulse data Pi, and the image features of the eye are transmitted to the image processing apparatus 10.

Figure 1:
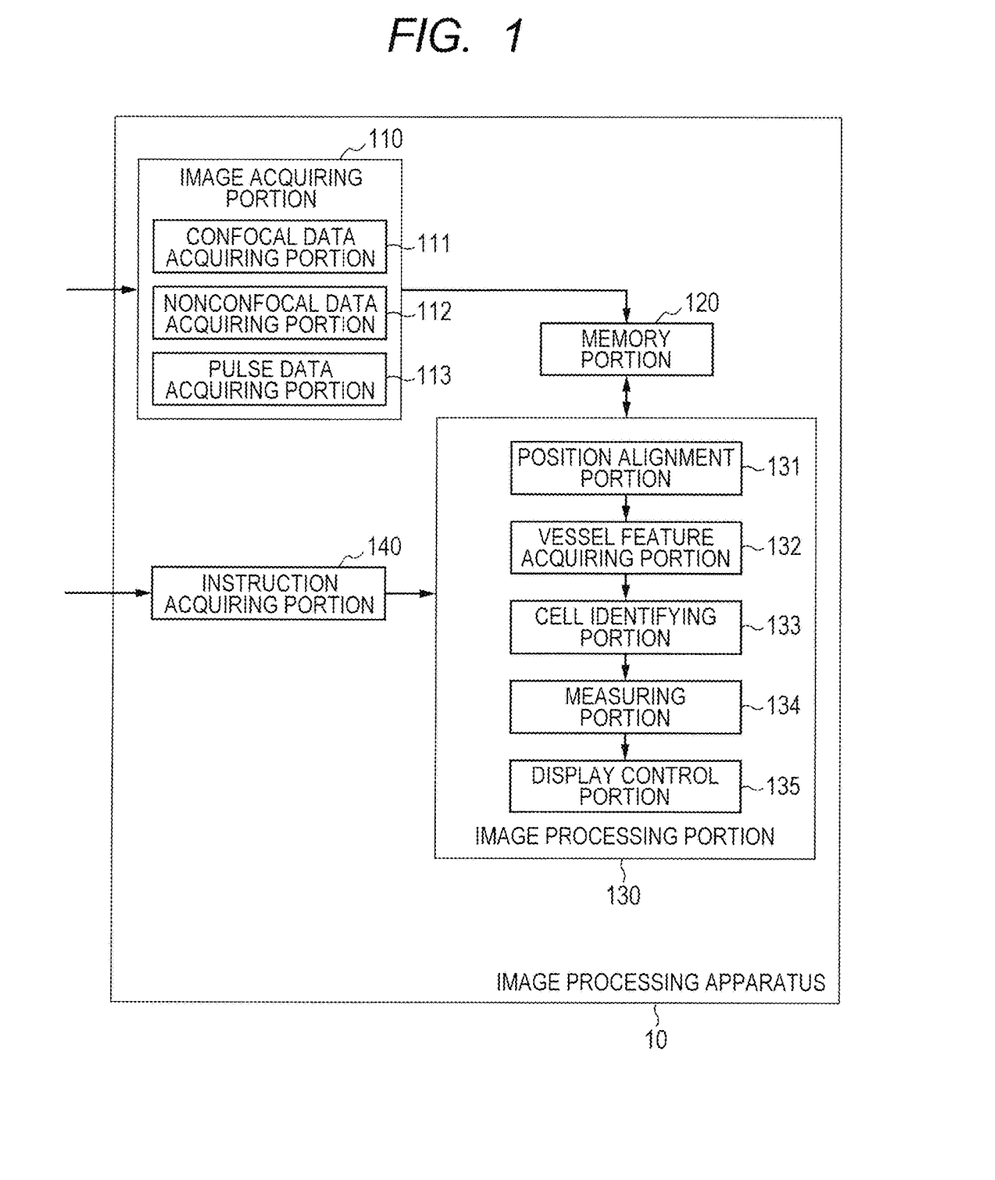
FIG. 1 is a block diagram for illustrating a configuration example of functions of an image processing apparatus according to a first embodiment of the present invention.

Next, a functional configuration of the image processing apparatus 10 according to this embodiment is described with reference to FIG. 1. FIG. is a block diagram for illustrating the functional configuration of the image processing apparatus 10, and the image processing apparatus 10 includes an image acquiring portion 110, a memory portion 120, an image processing portion 130, and an instruction acquiring portion 140. Further, the image acquiring portion 110 includes a confocal data acquiring portion 111, a nonconfocal data acquiring portion 112, and a pulse data acquiring portion 113. The image processing portion 130 includes a position alignment portion 131, a vessel feature acquiring portion 132, a cell identifying portion 133, a measuring portion 134, and a display control portion 135. Actual functions of those portions are described later.

Next, the SLO image acquiring apparatus 20 to which adaptive optics used in this embodiment is applied is described with reference to FIG. 3A and FIG. 3B. The SLO image acquiring apparatus 20 includes a super luminescent diode (SLD) 201, a Shack-Hartmann wavefront sensor 206, an adaptive optics system 204, a first beam splitter 202, a second beam splitter 203, an X-Y scanning mirror 205, a focus lens 209, an aperture portion 210, a photosensor 211, an image forming portion 212, and an output portion 213. The first beam splitter 202, the second beam splitter 203, the adaptive optics system 204, and the X-Y scanning mirror 205 are arranged in the stated order from the SLD 201 to an eye to be inspected. The focus lens 209, the aperture portion 210, and the photosensor 211 are arranged in the stated order in a branching direction of the first beam splitter 202. The image forming portion 212 is connected to the photosensor 211, and the output portion 213 is connected to the image forming portion 212. The Shack-Hartmann wavefront sensor 206 is arranged in a branching direction of the second beam splitter 203.

Measuring light emitted from the SLD 201 serving as a light source passes through an optical path in which the respective optical members are arranged and a crystalline lens OL of an eye E to be inspected to reach a fundus Er of the eye E to be inspected. The measuring light reflected by the fundus Er of the eye follows the optical path backward as return light. A part of return light is split toward the Shack-Hartmann wavefront sensor 206 by the second beam splitter 203. The other part of the return on light is further split by the first beam splitter 202 to be guided to the photosensor 211.

The Shack-Hartmann wavefront sensor 206 is a device for measuring an aberration of the eye, and has a CCD 208 connected to a lens array 207. The split part of the return light is transmitted through the lens array 207 as incident light. The incident light transmitted through the lens array 207 appears as a group of bright spots on the CCD 208, and a wavefront aberration of the return light is measured based on a positional deviation of the projected bright spots.

The adaptive optics system 204 drives an aberration correction device (not shown) to correct the aberration based on the wavefront aberration measured by the Shack-Hartmann wavefront sensor 206. The aberration correction device (not shown) is formed of a shape variable mirror or a spatial light phase modulator. The return light subjected to aberration correction and split by the first beam splitter 202 passes through the focus lens 209 and the aperture portion 210 to be received by the photosensor 211.

The scan position of the measuring light on the fundus Er of the eye can be controlled by moving the X-Y scanning mirror 205. By the control of the X-Y scanning mirror 205, the operator acquires data on an image acquisition target region specified in advance at a specified frame rate by a specified number of frames. The data is transmitted to the image forming portion 212, and subjected to the correction of an image distortion ascribable to variations in scanning speed and the correction of the brightness value, and image data (moving image or still image) is thus formed. The output portion 213 outputs the image data formed by the image forming portion 212 to the image processing apparatus 10 or the like.

Figure 3A:
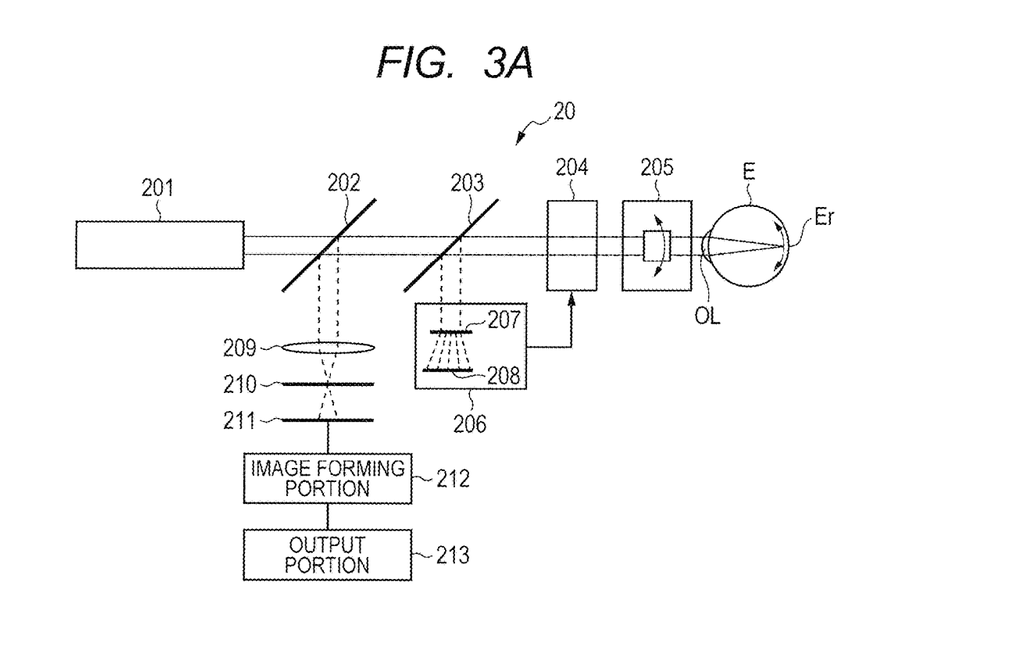
FIG. 3A is a diagram for illustrating an overall configuration of an SLO image acquiring apparatus according to the embodiment of the present invention.
Figure 3B:
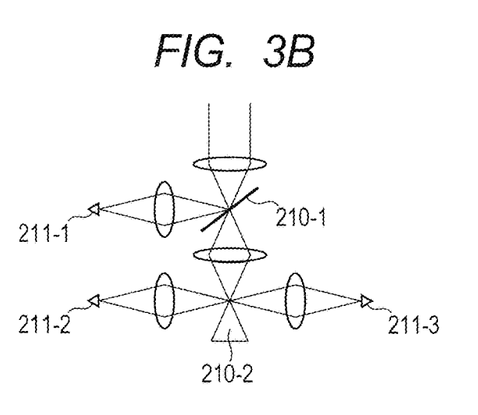
FIG. 3B is a diagram for illustrating an example of configurations of an aperture portion and a photosensor within the SLO image acquiring apparatus illustrated in FIG. 3A.

In this case, in the SLO image acquiring apparatus 20, the part of the aperture portion 210 and the photosensor 211 illustrated in FIG. 3A may have any configuration that can acquire the confocal image Dc and the nonconfocal image Dn. In this embodiment, the part of the aperture portion 210 and the photosensor 211 is formed of a light shielding portion 210-1 illustrated in FIG. 3B and FIG. 3E and photosensors 211-1, 211-2, and 211-3 illustrated in FIG. 3B. In FIG. 3B, the return light enters the light shielding portion 210-1 arranged on an imaging surface, and partial light thereof is reflected by the light shielding portion 210-1 to enter the photosensor 211-1.

Figure 3C:
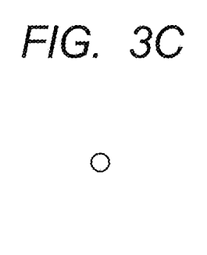
FIG. 3C is a diagram for illustrating an example of the aperture portion illustrated in FIG. 3B.
Figure 3D:
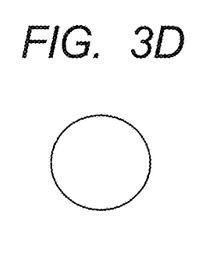
FIG. 3D is a diagram for illustrating an example of the aperture portion illustrated in FIG. 3B.
Figure 3E:
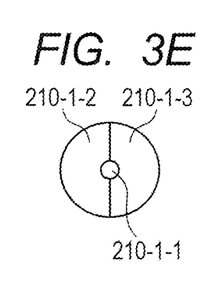
FIG. 3E is a diagram for illustrating an example of a light shielding portion illustrated in FIG. 3B.

Now, the light shielding portion 210-1 is described with reference to the FIG. 3E. The light shielding portion 210-1 is formed of transmission regions 210-1-2 and 210-1-3, a light shielding region (not shown), and a reflection region 210-1-1. The center of the light shielding portion 210-1 where the reflection region 210-1-1 is formed is arranged so as to be positioned at the center of an optical axis of the return light. Further, the light shielding portion 210-1 has an elliptical pattern that is formed into a circle when viewed from an optical axis direction when the light shielding portion 210-1 is arranged diagonally with respect to the optical axis of the return light.

The light split by being reflected by the reflection region 210-1-1 of the light shielding portion 210-1 enters the photosensor 211-1. The light that has passed through the transmission regions 210-1-2 and 210-1-3 of the light shielding portion 210-1 is further split by a two-split prism 210-2 arranged on the imaging surface. Light beams obtained after the splitting enter the photosensors 211-2 and 211-3, respectively, as illustrated in FIG. 3B.

A voltage signal obtained by each of the photosensors is converted into a digital value by an AD board included in the image forming portion 212, and then converted into a two-dimensional image. An image generated based on the light having entered the photosensor 211-1 becomes a confocal image focused within a particular narrow range. Further, an image generated based on the light input to the photosensors 211-2 and 211-3 becomes a nonconfocal image focused within a wide range.

Figure 3F:
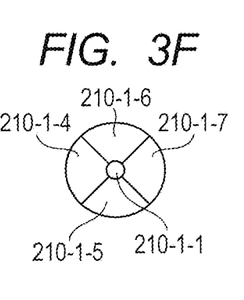
FIG. 3F is a diagram for illustrating an example of the light shielding portion illustrated in FIG. 3B.
Figure 3G:
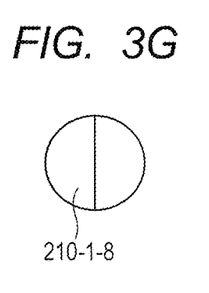
FIG. 3G is a diagram for illustrating an example of the light shielding portion illustrated in FIG. 3B.
Figure 3H:
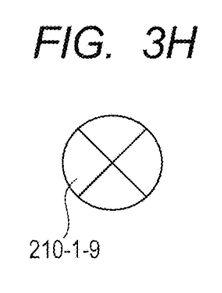
FIG. 3H is a diagram for illustrating an example of the light shielding portion illustrated in FIG. 3B.

Note that, a method of splitting the return light for extracting a nonconfocal signal is not limited thereto. For example, as illustrated in FIG. 3F, the transmission region may be divided into four (210-1-4, 210-1-5, 210-1-6, and 210-1-7) to obtain four nonconfocal signals. Further, a method of receiving a confocal signal and the nonconfocal signal is not limited thereto. For example, the diameter and position of the aperture portion 210 may be made variable and adjusted so as to receive the confocal signal under the state of an opening diameter of FIG. 3C and receive the nonconfocal signal under the state of an opening diameter of FIG. 3D. The diameter and moving amount of the aperture portion 210 may be set arbitrarily. For example, in FIG. 3C, the diameter of the aperture portion 210 can be set to 1 airy disc diameter (ADD), while in FIG. 3D, the diameter of the aperture portion 210 can be set to about 10 ADD, and the moving amount can be set to about 6 ADD. In another case, the light shielding portion 210-1 may be configured so that a plurality of nonconfocal signals are received substantially simultaneously by, for example, an aperture portion 210-1-8 divided into two as illustrated in FIG. 3G or an aperture portion 210-1-9 divided into four as illustrated in FIG. 3H. Note that, when the aperture portion 210 is divided into four, a four-split prism is arranged on the imaging surface in place of the two-split prism, and four photosensors are arranged as well.

In this embodiment, there are two kinds of nonconfocal signals, and hence one is represented by Dnr in the sense of an R-channel image, while the other is represented by Dnl in the sense of an L-channel image. The expression "nonconfocal image Dn" represents both the R-channel image Dnr and the L-channel image Dnl.

Note that, the SLO image acquiring apparatus 20 according to this embodiment may also be instructed to increase a swing angle of the X-Y scanning mirror 205 serving as a scanning optical system in the configuration of FIG. 3A to inhibit the adaptive optics system 204 from correcting the aberration. Such an instruction allows the SLO image acquiring apparatus 20 to operate also as a normal SLO apparatus to acquire a wide field angle image.

Note that, in the following, the image having a magnification lower than a high magnification images Dc and Dn and having the lowest magnification among the images acquired by the image acquiring portion 110 is referred to as the wide field angle image Dl (Dlc and Dln). Therefore, the wide field angle image Dl may be an SLO image to which the adaptive optics is applied, or may be a mere SLO image. Note that, a confocal wide field angle image and a nonconfocal wide field angle image are represented by Dlc and Dln, respectively, when distinguished from each other.

Figure 4:
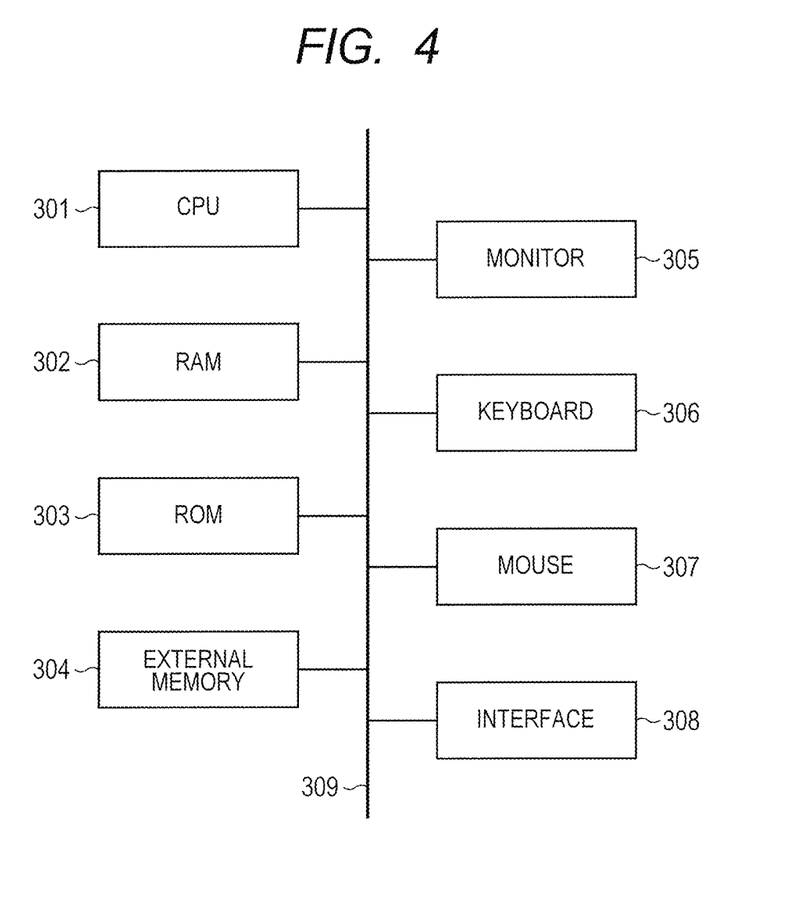
FIG. 4 is a block diagram for illustrating a hardware configuration example of a computer including hardware corresponding to a memory portion and an image processing portion and being configured to hold and execute other respective portions as software.

Next, a hardware configuration of the image processing apparatus 10 according to this embodiment is described with reference to FIG. 4. As illustrated in FIG. 4, the image processing apparatus 10 includes a central processing unit (CPU) 301, a memory (RAM) 302, a control memory (ROM) 303, an external memory 304, a monitor 305, a keyboard 306, a mouse 307, and an interface 308. Control programs for implementing image processing functions according to this embodiment and data to be used when the control programs are executed are stored in the external memory 304. Those control programs and the data are appropriately loaded into the RAM 302 through a bus 309 under the control of the CPU 301, and are executed by the CPU 301 to function as the respective portions described below.

Figure 5:
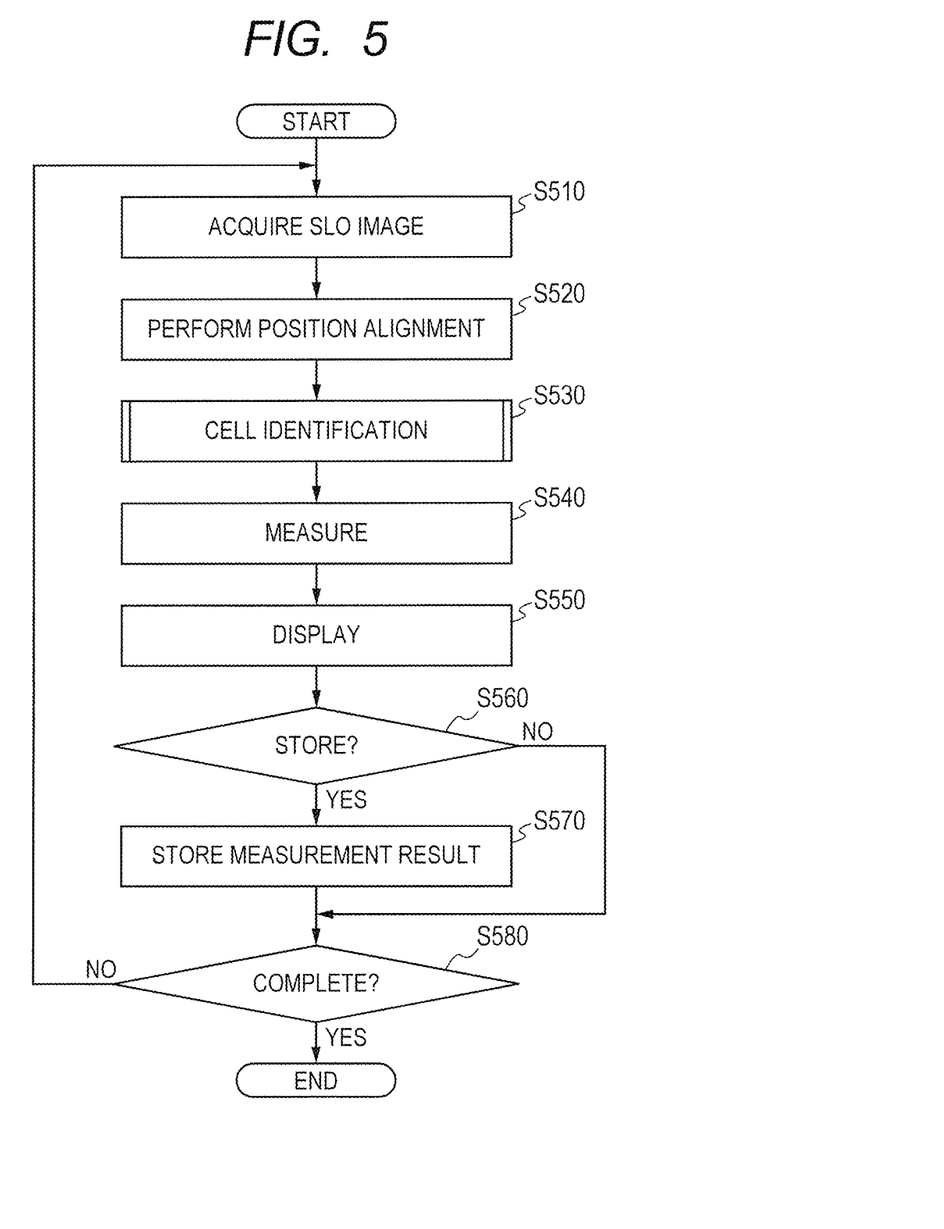
FIG. 5 is a flowchart of processing executed by the image processing apparatus according to the embodiment of the present invention.

The functions of the respective blocks that form the image processing apparatus 10 are described in association with a specific execution procedure of the image processing apparatus 10 illustrated in the flowchart of FIG. 5. FIG. 5 is a flowchart relating to an operation performed when the image of a fundus of the eye to be inspected is processed by the image processing apparatus 10.

<Step S510>

The image acquiring portion 110 requests the SLO image acquiring apparatus 20 to acquire a low magnification image and a high magnification image. The low magnification image corresponds to the wide field angle image Dl as illustrated in FIG. 6G, and the high magnification image corresponds to the confocal image Dcj within an annular region of an optic papilla portion as indicated by a region Pt' of FIG. 6G, and two nonconfocal images Dnrk and Dnlk. Further, the image acquiring portion 110 requests the SLO image acquiring apparatus 20 to acquire the fixation target positions Fl and Fcn corresponding to those images as well.

In response to the acquisition request, the SLO image acquiring apparatus 20 acquires the wide field angle image Dl, the confocal image Dcj, the nonconfocal images Dnrk and Dnlk, corresponding attribute data, and the fixation target positions Fl and Fcn. After the acquisition, those pieces of data are transmitted to the image acquiring portion 110. The image acquiring portion 110 receives the data such as the wide field angle image Dl, the confocal image Dcj, the nonconfocal images Dnrk and Dnlk, the fixation target positions Fl and Fcn from the SLO image acquiring apparatus 20 through the LAN 30, and stores those pieces of data into the memory portion 120.

Further, the pulse data acquiring portion 113 requests the pulse data acquiring apparatus 50 to acquire the pulse data Pi relating to a biosignal. In this embodiment, a sphygmograph is used as the pulse data acquiring apparatus, and the pulse wave data Pi is acquired from a lobulus auriculae (ear lobe) of a subject. Here, the pulse wave data Pi is expressed by a point sequence having one axis indicating an acquisition time and the other axis indicating a pulse wave signal value measured by the sphygmograph. The pulse data acquiring apparatus 50 acquires and transmits the corresponding pulse data Pi in response to the acquisition request. The pulse data acquiring portion 113 receives the pulse wave data Pi as a pulse data, from the pulse data acquiring apparatus 50 through the LAN 30. The pulse data acquiring portion 113 stores the received pulse data Pi into the memory portion 120.

Based on the pulse data Pi acquired by the pulse data acquiring apparatus 50, the confocal data acquiring portion 111 or the nonconfocal data acquiring portion 112 starts acquiring an image. Cases conceivable as modes of the image acquisition include a case where the image acquisition is started in synchronization with a given phase of the pulse data Pi and a case where the acquisition of the pulse wave data Pi and the image acquisition are simultaneously started immediately after the image acquisition request. In this embodiment, the acquisition of the pulse data Pi and the image acquisition are started immediately after the image acquisition request.

Pieces of pulse data Pi on the respective images are acquired from the pulse data acquiring portion 113, and extreme values of the respective pieces of the pulse data Pi are detected to calculate a heart beat cycle and a relative cardiac cycle. Note that, the relative cardiac cycle is a relative value expressed by a floating-point number ranging from 0 to 1 when the heart beat cycle is set to 1.

Figure 6C:
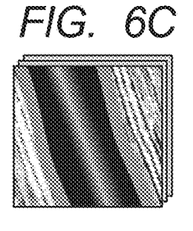
FIG. 6C is a diagram for illustrating an example of an obtained confocal image.
Figure 6D:
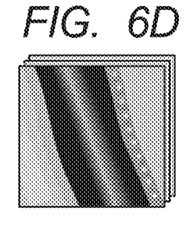
FIG. 6D is a diagram for illustrating an example of a nonconfocal image obtained regarding the same body part as that of the confocal image of FIG. 6C.
Figure 6E:
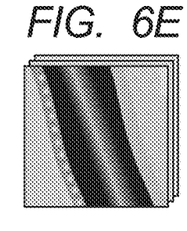
FIG. 6E is a diagram for illustrating an example of the nonconfocal image obtained regarding the same body part as that of the confocal image of FIG. 6C.

Now, examples of the confocal image Dc and the nonconfocal image Dnr obtained when the retinal vessel is imaged are illustrated in FIG. 6C and FIG. 6D. As illustrated in FIG. 6C, in the confocal image Dc, the reflection of a nerve fiber layer in a background thereof is strong, and position alignment easily becomes difficult due to noise in the background part. Further, as illustrated in FIG. 6D, in the nonconfocal image Dnr of the R-channel, the contrast of a blood vessel wall on the right is high. On the other hand, in the nonconfocal image Dnl of the L-channel, as illustrated in, for example, FIG. 6E, the contrast of a blood vessel wall on the left is high.

Figure 6F:
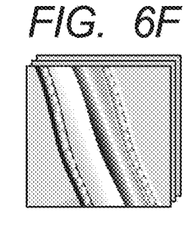
FIG. 6F is a diagram for illustrating an example of an image obtained based on FIG. 6D and FIG. 6E.
Figure 6G:
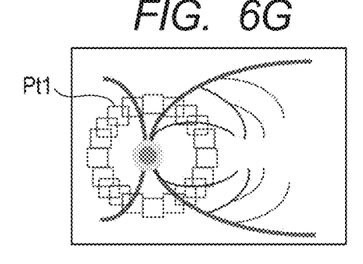
FIG. 6G is a diagram for illustrating a relationship between a low magnification image and a high magnification image.

Note that, as the nonconfocal image, any one of an addition-average image Dnr+l (FIG. 6H) and a split detector image Dns (FIG. 6F) can also be used as an image obtained by subjecting the R-channel image and the L-channel image to arithmetic operation processing. Through use of those images, the blood vessel wall may be observed, and measuring processing relating to the blood vessel wall may be performed. The addition-average image Dnr+l is an image obtained by subjecting the R-channel image and the L-channel image to addition averaging. Further, the split detector image Dns is an image obtained by performing difference emphasis processing ((L−R)/(R+L)) regarding the nonconfocal image.

Note that, the acquisition position of the high magnification image is not limited thereto, and the image in an arbitrary acquisition position may be used. For example, a case of using an image acquired in a macula portion or an image acquired along a retinal vessel arcade is also included in one embodiment of the present invention.

<Step S520>

The position alignment portion 131 serving as a position alignment unit performs inter-frame position alignment of the acquired images. Subsequently, the position alignment portion 131 determines an exceptional frame based on the brightness value and noise of each frame and a displacement amount with respect to a reference frame. Specifically, first, the inter-frame position alignment is performed for the wide field angle image Dl and the confocal image Dc. After that, a parameter value of the inter-frame position alignment is also applied to each of the nonconfocal images Dnr and Dnl.

Specifically, the inter-frame position alignment is executed by the position alignment portion 131 with the following procedure.
(i) The position alignment portion 131 first sets the reference frame as the reference of the position alignment. In this embodiment, the frame having the smallest frame number is set as the reference frame. Note that, a method of setting the reference frame is not limited thereto, and an arbitrary setting method may be used.
(ii) The position alignment portion 131 performs rough association of positions between frames (rough position alignment). An arbitrary position alignment method can be used therefor, but in this embodiment, a correlation coefficient is used as an inter-image similarity evaluation function, and affine transformation is used as a coordinate transformation method, to thereby perform the rough position alignment.
(iii) The position alignment portion 131 performs fine position alignment based on data on a correspondence relationship of the rough positions between the frames. In that case, in this embodiment, the fine position alignment between the frames is performed for a moving image obtained by being subjected to the rough position alignment in the stage (ii) through use of the free form deformation (FFD) method that is a kind of non-rigid position alignment method.

Note that, a method for the fine position alignment is not limited thereto, and an arbitrary position alignment method may be used. Further, in this embodiment, a position alignment parameter obtained by performing the inter-frame position alignment of the confocal image Dc is also used as a parameter for the inter-frame position alignment of the nonconfocal image Dn. However, an execution order or the like of the position alignment is not limited thereto. For example, a case of using a position alignment parameter obtained by performing the inter-frame position alignment of the nonconfocal image Dn as a parameter for the inter-frame position alignment of the confocal image Dc is also included in one embodiment of the present invention. In this case, it is preferred that the nonconfocal image Dn include not only Dnr and Dnl described above but also an image obtained by performing arithmetic operation processing for Dnr and Dnl.

Subsequently, the position alignment portion 131 performs the position alignment of the wide field angle image Dl and the high magnification confocal image Dcj (so-called merging of images), and obtains the relative position of the confocal image Dcj on the wide field angle image Dl. In this embodiment, the merging processing is performed through use of superimposed images of the respective moving images. In addition, the merging processing may be performed through use of, for example, the reference frames of the respective moving images. The position alignment portion 131 acquires the fixation target position Fcn used at the time of the image acquisition of the confocal image Dcj from the memory portion 120, and sets the fixation target position Fcn as an initial search point of the position alignment parameter for the position alignment of the wide field angle image Dl and the confocal image Dcj. From then on, the wide field angle image Dl and the confocal image Dcj are subjected to the position alignment while a combination of the parameter values is changed.

The combination of the position alignment parameter values having the highest similarity between the wide field angle image Dl and the confocal image Dcj is determined as the relative position of the confocal image Dcj on the wide field angle image Dl. Note that, the position alignment method is not limited thereto, and an arbitrary position alignment method may be used.

Further, when the image having a medium magnification is acquired in Step S510, the position alignment is performed in ascending order of the magnification from the image having the lowest magnification. For example, when the high magnification confocal image Dc1$m$ and the medium magnification confocal image Dc2$o$ are acquired, it is preferred that the position alignment be first performed between the wide field angle image Dl and the medium magnification image Dc2$o$. In this case, it is preferred that the above-mentioned position alignment be followed by the position alignment between the medium magnification image Dc2$o$ and the high magnification image Dc1$m$.

In addition, an image merging parameter value determined for the wide field angle image Dl and the confocal image Dcj is also applied to the merging of the nonconfocal images (Dnrk and Dnlk). Therefore, the relative positions of the high magnification nonconfocal images Dnrk and Dnlk on the wide field angle image Dl are respectively determined.

<Step S530>

The vessel feature acquiring portion 132 that functions as a vessel feature acquiring unit and the cell identifying portion 133 that functions as a cell identifying unit identify cells that form the blood vessel wall with the following procedure. That is, the cell identifying unit identifies the cells that form the blood vessel wall based on membrane candidate points that form an arbitrary wall within the blood vessel acquired by the vessel feature acquiring portion 132.
(i) A smoothing process is performed for the nonconfocal image having undergone the inter-frame position alignment in Step S520.
(ii) A morphology filter is applied to detect a retinal artery center line. In each position on the artery center line, the brightness profile on a line segment orthogonal to the artery center line is generated. Then, in regard to the brightness profile, local maximum values are detected at three points from the center of the line segment toward each of the left side and the right side, and are set as candidates for an intima, a media, and an adventitia of the blood vessel wall in the stated order from the position closest to the blood vessel center line. However, it is assumed that the membrane candidate points are not acquired from the brightness profile when the number of detected local maximum points is smaller than three. In addition, membrane candidate points for the media are interpolated along the travel direction of the wall, to thereby generate a curved line along the travel of a blood vessel wall.

(iii) The brightness profile is generated along the curved line generated in the stage (ii). The brightness profile is subjected to a Fourier transform, and then a low-pass filter is applied to a frequency domain, to thereby remove high frequency noise.

(iv) The local maximum values are detected on the brightness profile generated along the travel of the blood vessel wall, which is generated in the stage (iii), to identify cell positions. That is, the cells are identified based on the brightness profile generated along the sequence of the acquired membrane candidate points. The brightness profile can also be generated along a curved line parallel with the blood vessel center line arranged within a blood vessel wall region.

Figure 7:
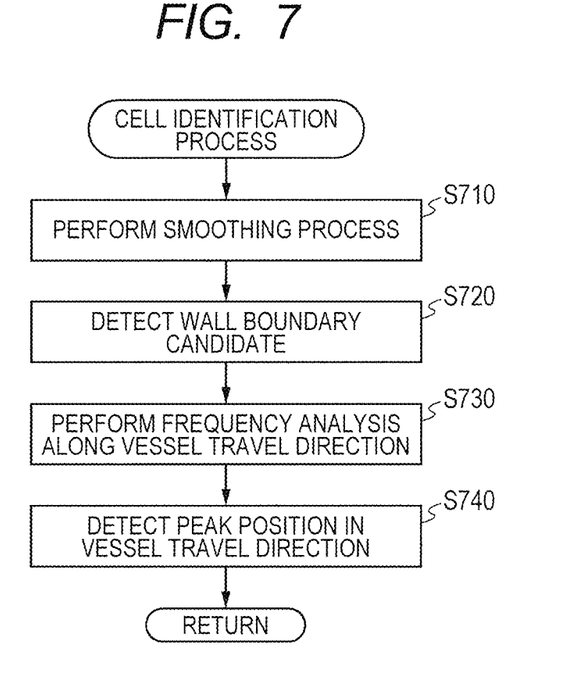
FIG. 7 is a flowchart for illustrating details of a cell identification process illustrated in the processing of FIG. 5.

Note that, a specific cell identification process is described in detail with reference to Step S710 to Step S740 illustrated in the flowchart of FIG. 7.

<Step S540>

The measuring portion 134 measures the distribution of the cells based on the positions of the cells that form the blood vessel wall which are identified in Step S530.

Specifically, mean values, standard deviations, maximum values, and minimum values are respectively calculated for a density of the detected existing cells that form the blood vessel wall, a distance between the adjacent cells, and an area occupied by the cells that form the blood vessel wall. In this embodiment, the positions of the cells in the media are identified to measure the cell density, the distance between the cells, and the area of the cells, but the present invention is not limited thereto. For example, the cell positions may be identified for each of the intima, the media, and the adventitia, and the cell density, the distance between the cells, and the area occupied by the cells may be calculated for each membrane. Note that, the density of cells that form the blood vessel wall is calculated as the number of existing cells within a predetermined membrane per unit distance. Those indices are calculated not only for the entire image, but also in units of a blood vessel branch, units of one side within the blood vessel branch (right side or left side in terms of the vessel travel direction), or units of a small region.

Note that, an index regarding the distribution of the cells that form the blood vessel wall is not limited thereto, and the index may be calculated by subjecting the cell densities calculated for a plurality of membranes to an arithmetic operation. For example, the following methods (a) or (b) may be exemplified.

(a) (Cell density in the media)/(cell density in the intima) is used as an index. That is, the density of the cells in the media that easily alter or die is standardized with the density of the cells in the intima that relatively hardly change.

(b) A cell density ratio within a predetermined membrane between the left side wall and the right side wall in terms of the vessel travel direction is set as an index.

The wall cells travel in a coil shape, and when a cell distribution abnormality occurs, the cell distribution abnormality is considered to be liable to occur on both sides. Therefore, the cell density ratio is used as the index of reliability regarding the detection result of the cells.

Further, the measurement involving the distribution of the cells is not limited to the above-mentioned contents (cell density, distance between the cells, and area of the cells). For example, it is conceivable that an arrangement of the cells is disturbed (line obtained by connecting the centers of the cells to each other becomes a broken line) in a case where the area occupied by the cells varies greatly even when the respective cells have not died. In such a case, as illustrated in FIG. 6K, wall cells Cn−1, Cn, and Cn+1 adjacent to each other are positioned without being aligned in a straight line. In this case, the distribution of an angle $\theta mi$ formed by line segments obtained by connecting the center positions to each other (line segment connecting Cn−1 and Cn and line segment connecting Cn and Cn+1), namely, the arrangement of the cells, may be measured. Also in this case, for example, a relative angle with respect to the vessel travel direction (value obtained by subtracting an angle ($\theta ci$) formed by the line segments between control points on the blood vessel center lines from the angle ($\theta mi$) between the centers of the adjacent cells on the wall as illustrated in FIG. 6K, or by dividing the angle ($\theta mi$) by the angle ($\theta ci$)) may be obtained.

Figure 6H:
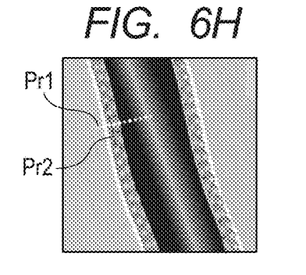
FIG. 6H is a diagram for illustrating another example of the image obtained based on FIG. 6D and FIG. 6E.
Figure 6I:
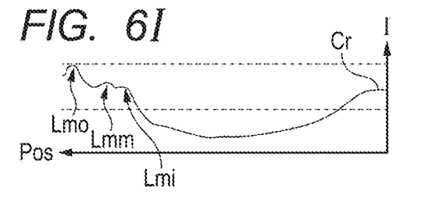
FIG. 6I is a graph for showing an example of a brightness profile along a line segment orthogonal to a blood vessel center line exhibited in respective positions on the blood vessel center line.
Figure 6J:
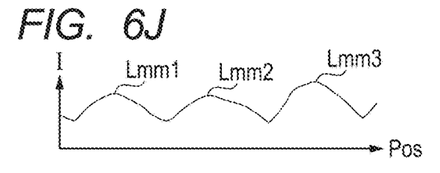
FIG. 6J is a graph for showing processing for searching a corrected brightness profile for a local maximum value of a brightness value.
Figure 6K:
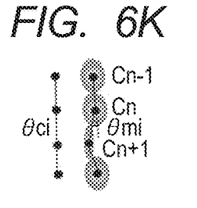
FIG. 6K is a diagram for illustrating an example of a method of measuring a cell distribution.
Figure 6L:
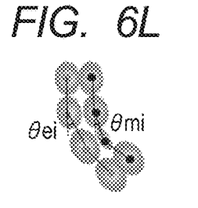
FIG. 6L is a diagram for illustrating another example of the method of measuring the cell distribution.

In another case, an angle obtained by performing subtraction or division for the angles between the centers of the cells, which are calculated for the respective membranes, between different membranes (value obtained by subtracting the angle $\theta ei$ between the centers of the cells in the intima from the angle $\theta mi$ between the centers of the cells in the media illustrated in, for example, FIG. 6L, or dividing the angle $\theta mi$ by the angle $\theta ei$) may be calculated as the relative angle between the different membranes.

That is, it is preferred that the arrangement of the cells be added to the area of the cells that form the blood vessel wall, the distance between the cells, and the density of existing cells as at least one item to be measured by the measuring portion 134 that functions as a measuring unit. Further, as described above, the measuring portion 134 calculates a specification value obtained by performing an arithmetic operation for the indices regarding the distribution of the cells measured for different membranes.

<Step S550>

Figure 8A:
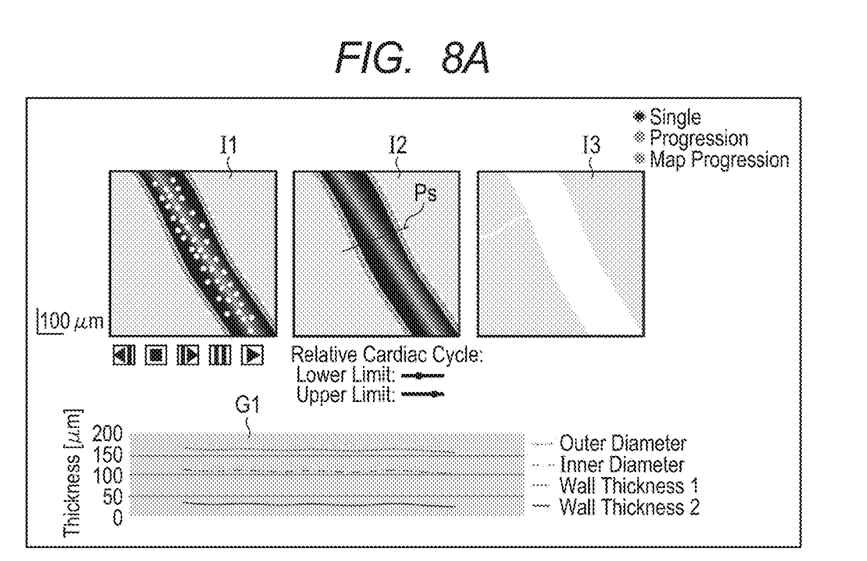
FIG. 8A is a diagram for illustrating content such as a measurement result displayed on a monitor in the processing illustrated in FIG. 5.
Figure 8B:
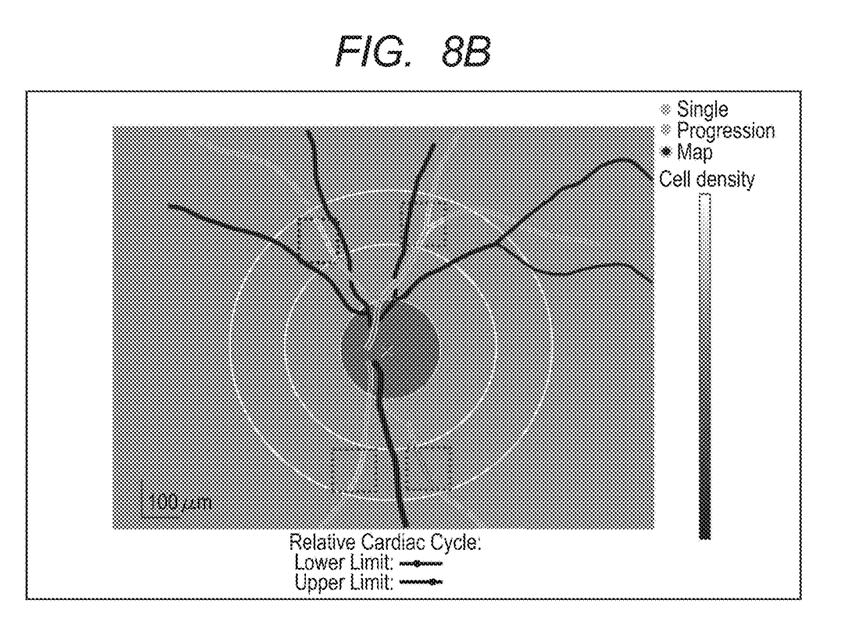
FIG. 8B is a diagram for illustrating a map displayed on the monitor in the processing illustrated in FIG. 5.

The display control portion 135 displays the acquired images, the detected positions of the wall cells, and a measurement result (wall cell density, distance between the cells, and area of the cells) on the monitor 305. In this embodiment, the following items (i) to (iv) are displayed. That is, (i) a nonconfocal moving image (II in FIG. 8A);
   an image processed by selecting and superimposing a frame corresponding to a particular phase of a pulse wave (12 in FIG. 8A); and
   an image obtained by extracting the lumen of the blood vessel (13 in FIG. 8A), which are displayed side by side,
(ii) a map of the detection positions of the cells that form the wall,
(iii) graphs indicating the cell density, the wall thickness, and the membrane thickness measured along the travel of the blood vessel wall ($\theta 1$ in FIG. 8A), and
(iv) a map for showing the distribution of the wall cells (wall cell density and area of the cells) calculated for each small area (FIG. 8B)

are displayed on the monitor 305. Note that, it is preferred that the item (iv) be displayed in colors after the calculated values are associated with a color bar.

<Step S560>

The instruction acquiring portion 140 acquires from the outside an instruction as to whether or not to store the images acquired in Step S510 and the data on the measurement result obtained in Step S540, that is, the values of the positions of the wall cells within the nonconfocal image Dnk, the wall cell density, and the like, in the data server 40. The instruction is input by the operator through, for example, the keyboard 306 and the mouse 307. When the storing is instructed, the processing advances to Step S570, and when the storing is not instructed, the processing advances to Step S580.

<Step S570>

The image processing portion 130 transmits an inspection date/time, information for identifying the eye to be inspected, and the images and the data on the measurement result, which are determined to be stored in Step S560, to the data server 40 in association with one another.

<Step S580>

The instruction acquiring portion 140 acquires from the outside an instruction as to whether or not to complete the processing relating to the high magnification nonconfocal image Dnk performed by the image processing apparatus 10. The instruction is input by the operator through the keyboard 306 and the mouse 307. When the instruction to complete the processing is acquired, the processing is brought to an end. Meanwhile, when the instruction to continue the processing is acquired, the processing returns to Step S510 to perform the processing for the next eye to be inspected (or reprocessing for the same eye to be inspected).

Further, the processing executed in Step S530 is described in detail with reference to the flowchart illustrated in FIG. 7.

<Step S710>

In order to identify the cells that form the blood vessel wall, the cell identifying portion 133 first performs an edge preserving smoothing process for the nonconfocal image. An arbitrary known edge preserving smoothing process is applicable, but in this embodiment, a median value filter is applied to the nonconfocal images Dnr+Dnl.

<Step S720>

The morphology filter is applied to the smoothed image generated by the cell identifying portion 133 in Step S710 to detect the retinal artery center line. In this embodiment, a top-hat filter is applied to detect a high brightness region having a narrow width, which corresponds to blood vessel wall reflection. Further, the high brightness region is subjected to a thinning process to detect the blood vessel center line. Note that, a method of detecting the blood vessel center line is not limited thereto, and an arbitrary known detection method may be used.

Subsequently, the cell identifying portion 133 generates a brightness profile Cr shown in FIG. 6I along a line segment (line segment Pr1 in FIG. 6H) orthogonal to the blood vessel center line in the respective positions on the blood vessel center line. Then, the brightness profile Cr is searched for the local maximum point from the center of the line segment toward the left side and the right side. Of the local maximum points, the first local maximum point Lmi having such a brightness value that a ratio or difference with respect to the brightness value on the center line falls within a predetermined range is set as a membrane candidate point for the intima, the second local maximum point Lmm is set as a membrane candidate point for the media, and the last local maximum point Lmo is set as a membrane candidate point for the adventitia. However, it is assumed that the membrane candidate points are not acquired from the brightness profile when the number of detected local maximum points is smaller than three. In addition, the local maximum point Lmm for the media detected from the brightness profile obtained in the respective positions on the blood vessel center line (along the line segment orthogonal to the blood vessels center line) is subjected to an interpolation process in the vessel travel direction. A membrane candidate point sequence for the media is generated through use of an interpolation value and a plurality of local maximum points aligned in the extending direction of the blood vessel center line, which are obtained above.

Note that, a method of acquiring the membrane candidate point sequence is not limited thereto, and an arbitrary known acquisition method may be used. For example, two curved lines parallel with the blood vessel center line are respectively arranged on a blood vessel lumen side and a nerve fiber side as a variable shape model. The model may be deformed so as to match a blood vessel wall boundary by minimizing an evaluation function value regarding the shape and the brightness value on the point sequence that forms the model, and the detected blood vessel wall boundary may be acquired as the membrane candidate point sequence.

<Step S730>

The cell identifying portion 133 generates a curved line through the interpolation of the membrane candidate point sequence generated in Step S720, and generates a brightness profile along the curved line (Pr2 in FIG. 6H).

Subsequently, the high frequency component is removed in order to remove a peak component other than the cells that form the wall (noise or light reflected from a fundus tissue other than the cells that form the wall) from the profile. In this embodiment, the frequency is transformed through use of a Fourier transform, and a low-pass filter is applied to cut a signal value of the higher frequency component. The filtered signal is returned to a spatial domain by being subjected to an inverse Fourier transform, to generate a corrected brightness profile with the high frequency components removed therefrom.

<Step S740>

The cell identifying portion 133 detects the local maximum values (Lmm1, Lmm2, and Lmm3 in FIG. 6J) through the search for the brightness value on the corrected brightness profile generated in Step S730. Based on the obtained local maximum values, the cell positions along the vessel travel direction are identified.

According to the above-mentioned configuration, the image processing apparatus 10 detects the extreme values and the brightness profile along the travel of the wall from the image acquired by imaging the retinal vessel wall through the use of the SLO apparatus configured to simultaneously acquire the confocal image and the nonconfocal image, to thereby detect the cells that form the blood vessel wall and automatically measure the distribution of the cells.

With this configuration, the distribution of the cells that form the blood vessel wall of the eye is simply and accurately measured.

OTHER EMBODIMENTS

The description of the above-mentioned embodiment is directed to the case where the image acquiring portion 110 includes both the confocal data acquiring portion 111 and the nonconfocal data acquiring portion 112. However, the image acquiring portion 110 does not necessarily include the confocal data acquiring portion 111 as long as the configuration allows the acquisition of at least two kinds of nonconfocal data.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-062507, filed Mar. 25, 2015, which is hereby incorporated by reference herein in its entirety.

REFERENCE SIGNS LIST 110 image acquiring portion
132 vessel feature acquiring portion
133 cell identifying portion

The invention claimed is:

1. An image processing apparatus, comprising:
at least one of (a) a processor and (b) circuitry, configured to function as units comprising:
(1) an image acquiring unit configured to acquire an image of an eye, the image including a cross-section of a blood vessel wall;
(2) an acquiring unit configured to acquire candidate points of a membrane of a blood vessel wall from the acquired image, the candidate points of the membrane including candidate points of a media of the blood vessel wall; and
(3) a cell identifying unit configured to identify cells within the media of the blood vessel wall based on the candidate points of the media.

2. The image processing apparatus according to claim 1, wherein the cell identifying unit is configured to identify the cells within the media based on a brightness profile generated along a sequence of the acquired candidate points.

3. The image processing apparatus according to claim 1, wherein the at least one of (a) a processor and (b) circuitry is further configured to function as a measuring unit configured to perform measurement relating to at least one of an area of the cells of the blood vessel wall, a distance between the cells, a density of existing cells, or an arrangement of the cells, based on the identified cells.

4. The image processing apparatus according to claim 3, wherein the measuring unit is further configured to calculate a specification value obtained by performing an arithmetic operation for indices regarding a distribution of the cell measured for different membranes.

5. The image processing apparatus according to claim 1, wherein the at least one of (a) a processor and (b) circuitry is further configured to function as a position alignment unit configured to perform position alignment of a wide field angle image and a plurality of high magnification images of the eye, the wide field angle image and the plurality of high magnification images being acquired by the image acquiring unit, and
wherein the acquiring unit is configured to acquire the candidate points based on the plurality of high magnification images subjected to the position alignment.

6. The image processing apparatus according to claim 5, wherein the plurality of high magnification images comprise a confocal image and a nonconfocal image, and
wherein the position alignment unit is further configured to perform the position alignment of the wide field angle image and the nonconfocal image through use of a parameter value used when the wide field angle image and the confocal image are subjected to the position alignment.

7. A non-transitory tangible medium having recorded thereon a program for causing a computer to operate as each unit of the image processing apparatus of claim 1.

8. An image processing method, comprising:
acquiring an image of an eye, the image including a cross-section of a blood vessel wall;
acquiring candidate points of a membrane of a blood vessel wall from the acquired image, the candidate points of the membrane including candidate points of a media of the blood vessel wall; and
identifying cells within the media of the blood vessel wall based on the candidate points of the media.

9. A non-transitory tangible medium having recorded thereon a program for causing a computer to execute each step of the image processing method of claim 8.

10. The image processing apparatus according to claim 3, further comprising a display unit configured to display a map based on at least one of the area of the cells of the blood vessel wall, the distance between the cells, the density of existing cells, or the arrangement of the cells.

* * * * *